US006624321B2

(12) United States Patent
Denninger et al.

(10) Patent No.: US 6,624,321 B2
(45) Date of Patent: Sep. 23, 2003

(54) PROCESS FOR THE PREPARATION OF POLYETHER POLYOLS

(75) Inventors: Uwe Denninger, Bergisch Gladbach (DE); Jörg Hofmann, Krefeld (DE); Pramod Gupta, Bedburg (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/277,615

(22) Filed: Oct. 22, 2002

(65) Prior Publication Data

US 2003/0097026 A1 May 22, 2003

Related U.S. Application Data

(60) Division of application No. 09/827,655, filed on Apr. 6, 2001, now Pat. No. 6,492,565, which is a continuation-in-part of application No. 09/411,065, filed on Oct. 4, 1999, now abandoned.

(30) Foreign Application Priority Data

Oct. 7, 1998 (DE) .......................................... 198 46 095

(51) Int. Cl.[7] .............................. C07F 5/06; C07F 5/02; B01J 31/00; C07C 41/03
(52) U.S. Cl. ............................ 556/177; 556/1; 556/21; 556/174; 556/182; 568/6; 568/618; 568/620; 526/266; 526/273; 502/152
(58) Field of Search ................................ 556/174, 177, 556/182, 1, 21; 502/152; 526/266, 273; 568/618, 620

(56) References Cited

U.S. PATENT DOCUMENTS

| | | | |
|---|---|---|---|
| 4,029,879 A | 6/1977 | Muzzio | 536/4 |
| 4,129,718 A | 12/1978 | Muzzio | 536/4 |
| 4,482,750 A | 11/1984 | Hetzel et al. | 568/621 |
| 4,543,430 A | 9/1985 | Falgoux et al. | 568/678 |
| 4,721,816 A | 1/1988 | Edwards | 568/618 |
| 4,721,817 A | 1/1988 | Edwards | 518/618 |
| 5,342,903 A | 8/1994 | Wolleb et al. | 525/407 |
| 5,362,835 A | 11/1994 | Rolfe et al. | 528/87 |

FOREIGN PATENT DOCUMENTS

JP    73026391    8/1973

OTHER PUBLICATIONS

Ency. of Poly. Sci. 7 Eng., vol 6 (month unavailable) 1986, pp. 273–275, Propylene Oxide and Oxide and Higher 1,2–Epoxide Polymers.

*Primary Examiner*—Porfirio Nazario-Gonzalez
(74) *Attorney, Agent, or Firm*—Joseph C. Gil; N. Denise Brown

(57) ABSTRACT

The present invention relates to a process for the preparation of polyether polyols by the reaction of alkylene oxides and compounds containing active hydrogens, in the presence of specific Lewis acid metal compounds as catalysts, novel bis(perfluoroalkylsulfonic acid) compounds of Group 13 of the Periodic Table of the Elements, and to a process for the preparation thereof and the use thereof as catalysts for ring-opening polymerization of cyclic ethers.

10 Claims, No Drawings

PROCESS FOR THE PREPARATION OF POLYETHER POLYOLS

CROSS-REFERENCE TO RELATED APPLICATIONS

The present application is a divisional application of U.S. application Ser. No. 09/827,655, filed on Apr. 6, 2001, now U.S. Pat. No. 6,492,565, which is a continuation-in-part application of U.S. application Ser. No. 09/411,065, filed Oct. 4, 1999 now abandoned.

BACKGROUND OF THE INVENTION

The present invention relates to a process for the preparation of polyether polyols by the reaction of alkylene oxides and compounds containing active hydrogens in the presence of specific Lewis acid metal compounds as catalysts, novel bis(perfluoroalkylsulfonic acid) compounds of elements from Group 13 of the Periodic Table of the Elements and a process for the preparation thereof, and the use thereof as catalysts for ring-opening polymerization of cyclic ethers.

Polyether polyols can be produced by a polyaddition reaction between alkylene oxides such as, for example, ethylene oxide, propylene oxide, butylene oxide, and compounds containing active hydrogen atoms, such as alcohols, amines, acid amides, phenols, and are used, inter alia, for the preparation of polyurethane plastics, surfactants and lubricants. Industrial polyaddition reactions between epoxides and starting compounds generally takes place by alkali catalysis. The alkali catalysts predominantly used are alkali hydroxides. Disadvantages of alkali hydroxide catalyzed polyether polyol preparation include the long reaction times (i.e., >5 hours) and the labor-intensive working-up of the product which is necessitated by neutralization of the alkaline polymer. See, for example, U.S. Pat. Nos. 4,129,718, 4,482,750 and 4,029,879, J.P. Patent Number 73026391, Encyclopedia of Polymer Science & Eng., Vol. 6, New York 1986, pages 273 to 307). A further problem is the base-catalyzed rearrangement of epoxides, for example propylene oxide, to allyl or propenyl alcohols, which takes place as a side-reaction and leads to monofunctional polyethers having a terminal double bond.

Acid catalysis, in particular with Lewis acids such as, for example, boron trifluoride, has also long been known, in addition to basic catalysis, for polyaddition reactions between alkylene oxides and starting compounds. Acid catalysis for the preparation of polyether polyols has the disadvantages that side reactions (for example formation of volatile low molecular weight cyclic ethers) are favored to an increased degree, hydroxyl groups are substituted by acid anions, and the relative molar mass distribution of the polyols is broader than that which typically occurs when compared to similar products prepared by base catalysis. Further disadvantages are the difficulty of separating (Lewis) acid catalysts and their sensitivity to hydrolysis, which necessitates the use of special materials (for example enamels) in the reaction apparatus used. Furthermore, the high catalytic reactivity of acid catalysts makes the reaction difficult to control.

U.S. Pat. No. 4,543,430 describes a process for the monoalkoxylation of hydroxylized compounds in the presence of trifluoromethane sulfonic acid salts. The alcohol-epoxy ratio must always be $\geq 2$ in order to form only the monoaddition product.

A process for the preparation of polyethers by the reaction of diepoxides with dihydroxides in the presence of metal triflate salts is described in EP 493,916. The process requires deactivation of the catalyst.

In order to increase selectivity, EP-A 569,331 proposes a process for the preparation of additional products by the reaction of an alcohol with an epoxide compound, in which the catalysts comprises a complex metal compound of a metal from the main or subgroups of the Periodic Table of the Elements with sulfonate radicals of a perfluoro-containing, alkanesulfonic acid and at least one weakly bonded neutral, unidentate or multidentate ligand is used. A metal complex compound corresponding to the formula $La(CH_3CN)_x(H_2O)_y(CF_3SO_3)_3$ is particularly suitable for the latter process (see claim 12 of EP-A 569,331). Disadvantages of the latter metal complex catalysts with regard to the process for the preparation of polyether polyols include the difficulty of separating and recovering completely the complex system of metal perfluoroalkylsulfonate and ligands from the polyol reaction mixture, and the low catalytic activity of the latter metal complex compounds, such that large quantities of catalyst must be used for the process for the preparation of polyethers. Polyether preparation with the latter metal complex compounds would therefore be highly uneconomical.

U.S. Pat. Nos. 4,721,816 and 4,721,817 describe a process for the preparation of alkanol-alkoxylate products in the presence of catalysts which are obtained by the reaction of one or more aluminum compounds and a sulfur-containing or phosphorus-containing acid. This process is characterized in that corrosive acids are used which have the disadvantages described above. Furthermore, a two-component system, such as that described above, is very demanding as to precise dispensing of the two components. Comparative Examples show that the aluminum component alone has only very low catalytic activity.

It has surprisingly now been found that, without the simultaneous presence of ligands, accelerators or co-catalysts, specific metal compounds enable polyaddition reactions to take place between epoxides and starting compounds having active hydrogen atoms, with high selectivity and catalytic activity. These compounds in a catalytically active quantity show (even after hydrolysis) neutral to slightly acidic behavior. That is to say that these compounds have pH values of $\leq 7.0$. Consequently, it is possible to dispense with a neutralization of the catalyst at the end of the reaction.

SUMMARY OF THE INVENTION

The present invention therefore provides a process for the preparation of polyether polyols from alkylene oxides and starting compounds which contain active hydrogen atoms. This process is carried out in the presence of metal compounds which correspond to the general formula (I):

$$(X)_n M(E-R-E'_l)_m \qquad (I)$$

wherein:
X: represents a halide, thiolate, sulfinate, sulfonate, sulfate, amide, or carboxylate;
M: represents a metal from Group 13 of the Periodic Table of the elements;
E: represents oxygen, sulfur, selenium, $NR^1$ or $PR^1$;
  wherein:
  $R^1$: represents a hydrogen atom or a $C_1$–$C_{20}$ hydrocarbon radical, preferably a $C_1$–$C_{10}$ hydrocarbon radical, which may be alkyl or aryl;
R: represents a $C_1$–$C_{30}$ hydrocarbon bridge which may be an alkylene, an arylene or an aralkylene bridge, and wherein R can form one or more rings with $R^1$;

E': represent a hydrogen atom, a $C_1$–$C_{20}$ hydrocarbon radical, preferably a $C_1$–$C_{10}$ hydrocarbon radical, which may be alkyl or aryl, $OR^2$, $NR^2$, $R^3$, halogen, $SR^2$ or $PR^2R^3$, and wherein:

$R^2$ and $R^3$: are the same or different, and each independently represents a hydrogen atom or a $C_1$–$C_{10}$ hydrocarbon radical which may be alkyl, aryl or aralkyl, and wherein $R^2$ can form one or more rings with $R^3$ or R, and/or $R^3$ can form one or more rings with R or $R^2$, and/or two or more ERE' units can form one or more rings;

n: represents 1 or 2;

m: equals (3–n);

and

I: represents an integer from 1 to 10.

The process according to the invention is generally carried out at temperatures of from 40 to 200° C. and at total pressures of from 0 to 20 bar, and, optionally, in the presence of an inert organic solvent.

Examples of alkylene oxides which are used are $C_1$–$C_{20}$ alkylene oxides, preferably ethylene oxide, propylene oxide, butylene oxide and mixtures thereof. The building of the polyether chains by alkoxylation may be carried out with only one monomeric epoxide, but may also take place in either random or block manner with two or three different monomeric epoxides. Further details are to be found in "Ullmanns Encyclopädie der industriellen Chemie", English language edition. 1992, Vol. A21, pages 670 to 671.

Compounds containing active hydrogen atoms, including those compounds preferably having molecular weights of 18 to 400 and having 1 to 8 hydroxyl, thiol and/or amino groups are suitable as the starting compounds in accordance with the present invention. The following compounds may be named as examples: ethylene glycol, diethylene glycol, 1,2-propylene glycol, 1,4-butanediol, hexamethylene glycol, bisphenol A, trimethylolpropane, glycerol, pentaerythritol, sorbitol, cane sugar, degraded starch, water, methylamine, ethylamine, propylamine, butylamine, aniline, benzylamine, o- and p-toluidine, α,β-naphthylamine, ammonia, ethylene diamine, propylene diamine, 1,4-butylene diamine, 1,2-, 1,3-, 1,4-, 1,5- and/or 1,6-hexamethylene diamine, such as o-, m- and p-phenylene diamine, 2,4- and 2,6-tolylene diamine, 2,2'-, 2,4'- and 4,4'-diaminodiphenylmethane and diethylene diamine.

Halides, thiolates, sulfinates, sulfonates, amides or carboxylic acids are suitable as X in formula (I) above.

If X represents a halide, F, Cl, Br and I are considered as suitable examples for the present invention.

In formula (I) above, if X represents thiolate, then some examples of suitable thiols include compounds such as methylthiol, ethylthiol, n-propylthiol, 1-propylthiol, n-butylthiol, s-butylthiol, tert.-butylthiol, nonylthiol, decylthiol, dodecylthiol, hexadecylthiol, cyclohexylthiol, menthylthiol, neomenthylthiol, thiophenol, o-, m- or p-methylthiophenol, 2,4,6- or 3,4,5-trimethylthiophenol, α- or β-thionaphthol, 1- or 2-thioanthrol, benzylthiol, 2- or 3-methylbenzylthiol or 1-phenylethylthiol.

If X represents a sulfinate, then examples of suitable compounds include substituted alkylsulfinic or arylsulfinic acids such as, for example, methyl sulfinate, ethyl sulfinate, trifluoromethyl sulfinate or phenyl sulfinate.

If X represents a sulfonate, then examples of suitable compounds include substituted alkylsulfonic or arylsulfonic acids such as, for example, methanesulfonic acid, ethanesulfonic acid, propanesulfonic acid, butanesulfonic acid, pentanesulfonic acid, hexanesulfonic acid, dodecanesulfonic acid, hexadecanesulfonic acid, cyclohexylsulfonic acid, trifluoromethanesulfonic acid, tetrafluoroethanesulfonic acid, pentafluoroethanesulfonic acid, heptafluoropropanesulfonic acid, heptadecanefluoroctanesulfonic acid, benzenesulfonic acid, toluene-sulfonic acid or styrenesulfonic acid.

If X represents a sulfate, then examples of suitable sulfates include, compounds such as substituted monoalkyl sulfuric or monoaryl sulfuric acid esters, for example methylsulfuric acid, ethylsulfuric acid, trifluoromethylsulfuric acid or phenylsulfuric acid.

In formula (I), if X represents an amide, then some examples of suitable compounds include dimethylamide, diethylamide, dipropylamide, methylethylamide, methylpropylamide, diisopropylamide, di-tert.-butylamide, methylphenylamide, diphenylamide or methyinaphthylamide.

In formula (I), if X represents a carboxylate, then some examples of suitable carboxylates include substituted saturated or unsaturated aliphatic carboxylic acids such as acetic acid, trifluoroacetic acid, propionic acid, butyric acid, hexanoic acid, lauric acid, palmitic acid, acrylic acid, methacrylic acid, propiolic acid, crotonic acid, sorbic acid or oleic acid, cycloaliphatic carboxylic acids such as hexahydrobenzoic acid, aromatic carboxylic acids, such as benzoic acid, naphthoic acid or toluic acid, or araliphatic carboxylic acids such as hydrotropic acid, atropic acid or cinnamic acid.

The elements from Group 13 of the Periodic Table of the Elements, such as boron, aluminum, gallium, indium or thallium, for example, are suitable as M.

Oxygen (O), sulfur (S), selenium (Se), $NR^1$ or $PR^1$, wherein $R^1$ is hydrogen (H) or a $C_1$–$C_{20}$ hydrocarbon radical, preferably a $C_1$–$C_{10}$ hydrocarbon radical, that may be an alkyl group or an aryl group such as, for example, methyl, ethyl, tert.-butyl or phenyl, are suitable to be used as E.

E' may represent hydrogen (H), an alkyl-radical, an aryl-radical, a halogen, a $R^2O$ radical, a $R^2C(O)O$— radical, a $R^2S$— radical, a $R^2R^3N$— radical, a $R^2C(O)N(R^3)$— radical, a $R^2R^3P$— radical, a $O_2N$— radical, a $H(O)C$— radical, a $R^2(O)C$— radical, a $R^2O(O)C$— radical, a NC— radical, a $R^2OS(O)_2$— radical or a $R^2OS(O)_2$ radical. In accordance with the present invention, $R^2$ and $R^3$ may be the same or different, and each is independently selected from the group comprising a hydrogen atom (H), an alkyl radical, an aryl radical or an aralkyl radical. It is also possible that $R^2$ and $R^3$ are joined together to form one or more rings with one another.

In accordance with the present invention, alkylene, arylene and aralkylene bridges are suitable as R. Alkylene bridges are understood here to be, for example, structural units which satisfy the formula (II)

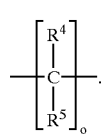

(II)

Here, $R^4$ and/or $R^5$ may be the same or different groups, and each is independently selected from the group consisting of a hydrogen atom (H), an alkyl radical, an aryl radical, a halide, an alkoxide and an aryl oxide. It is also possible that $R^4$ and $R^5$ can be joined together to form one or more rings with $R^1$, $R^2$, $R^3$, $R^4$ and/or $R^5$. It is also possible that $R^4$ and/or $R^5$ can also be coupled with $R^4$ and/or $R^5$ of adjacent carbon atoms, such that double or triple bonds exist between the two carbon atoms.

O in formula (II) above represents an integer having a value between 1 and 10.

Suitable alkoxides and aryl oxides to be used as $R^4$ and/or $R^5$ in formula (II) above are as described below.

In accordance with the present invention, arylene or aralkylene bridges are understood to be, for example, structural units which satisfy the following formulae (III) to (X) described below.

(III)
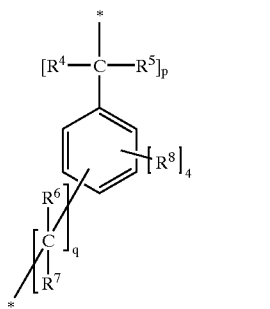

(IV)
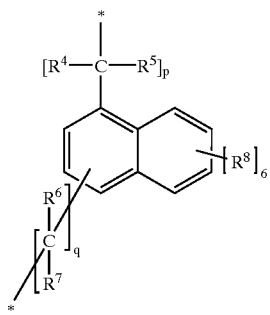

(V)
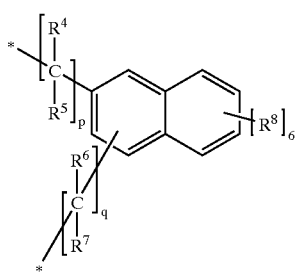

(VI)
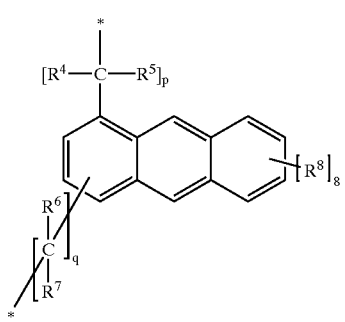

(VII)
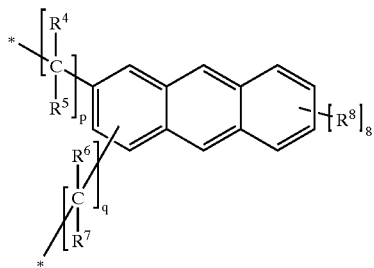

(VIII)
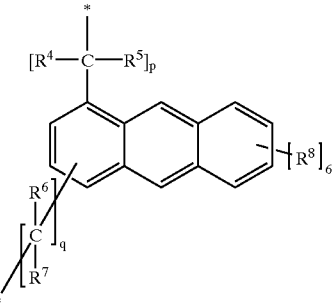

(IX)
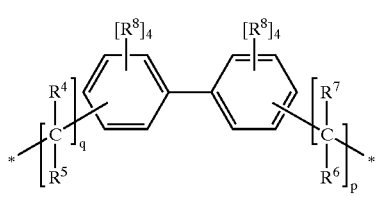

(X)
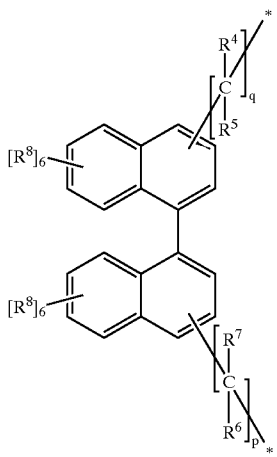

The positions marked with * identify the positions of the substituents E and E'. The location of E and E' in these positions may be reversed.

In formula (III) above, bridging may take place in the o-, m- or p-position in the benzene ring.

In formula (IV), bridging may take place in the 1,2-, 1,3-, 1,4-, 1,5-, 1,6-, 1,7- or 1,8-position in the naphthalene skeleton.

In formula (V), bridging may take place in the 2,3-, 2,4-, 2,5-, 2,6-, 2,7- or 2,8-position in the naphthalene skeleton.

In formula (VI), bridging may take place in the 1,2-, 1,3-, 1,4-, 1,5-, 1,6-, 1,7-, 1,8-, 1,9- or 1,10-position in the anthracene skeleton.

In formula (VII), bridging may take place in the 2,3-, 2,4-, 2,5-, 2,6-, 2,7-, 2,8-, 2,9- or 2,10-position in the anthracene skeleton.

In formula (VIII), bridging may take place in the 1,9-, 2,9-, 3,9-, 4,9- or 9,10-position in the anthracene skeleton.

In formula (IX) bridging may take place in the 2,2'-, 2,3'-, 2,4'-, 2,5'-, 2,6'-, 3,3'-, 3,4'-, 3,5'-, 3,6'-, 4,4'-, 4,5'-, 4,6'-, 5,5'-, 5,6'- or 6,6'-position in the biphenyl skeleton.

In formula (X), bridging may take place in the 2,2'-, 2,3'-, 2,4'-, 2,5'-, 2,6'-, 2,7'-, 2,8'-, 3,3'-, 3,4'-, 3,5'-, 3,6'-, 3,7'-, 3,8'-, 4,4'-, 4,5'-, 4,6'-, 4,7'-, 4,8'-, 5,5'-, 5,6'-, 5,7'-, 5,8'-, 6,6'-, 6,7'-, 6,8'-, 7,7'-, 7,8'- or 8,8'-position in the binaphthyl skeleton.

$R^6$ and/or $R^7$ may be the same or different, and each is independently selected from the group consisting of: a hydrogen (H) atom, an alkyl, an aryl, a halide, alkoxide and aryl oxide. $R^6$ and/or $R^7$ can form one or more rings by combining with $R^6$ and/or $R^7$. Halides here are defined as above. Alkoxides and aryl oxides here are defined as follows.

Examples of suitable alkoxides include saturated and unsaturated aliphatic alcohols such as, for example, methanol, ethanol, n-propanol, I-propanol, n-butanol, sec.-butanol, tert.-butanol, nonanol, decanol, dodecanol, hexadecanol, cyclohexanol, menthol and/or neomenthol.

Examples of suitable aryl oxides include compounds such as substituted phenols, naphthols, anthracenols or phenanthrenols such as, for example, phenol, o-, m- or p-methylphenol, 2,4,6- or 3,4,5-trimethylphenol, 2,6-di-tert.-butylphenol, 2,6-di-tert.-butyl-4-methylphenol, α- or β-naphthol, 1- or 2-anthrol or 9-hydroxyphenanthrene.

$R^4$ and/or $R^5$ in formulas (II) through (X) above can form one or more rings with $R^1$, $R^2$, $R^3$, $R^4$ and/or $R^5$. $R^6$ and/or $R^7$ can also be linked with $R^6$ and/or $R^7$ of adjacent Carbon atoms, such that double or triple bonds can be formed between the two C atoms.

Each $R^8$ group may be the same or different, and is independently selected from the group consisting of a hydrogen (H) atom, an alkyl radical, an aryl radical, an aralkyl radical, a halogen atom, $R^2O$, $R^2C(O)O$—, $R^2S$—, $R^2R^3N$, $R^2C(O)N(R^3)$, $R^2R^3P$—, $O_2N$—, $H(O)C$—, $R^2(O)C$—, $R^2O(O)C$—, NC—, $R^2S(O)_2$— or $R^2OS(O)_2$ groups.

$R^4$, $R^5$, $R^6$ and $R^7$ may be the same or different, and each is independently selected from the group comprising hydrogen (H), alkyl, aryl, halide, alkoxide or aryl oxide. $R^4$, $R^5$, $R^6$ and/or $R^7$ can form one or more rings by combining together with $R^1$, $R^2$, $R^3$ and/or with each other. Halides, alkoxides and aryl oxides herein are as defined above.

In formulas (III) through (X) above, the letters p and q represent integers from 0 to 8 and may be either the same or different. The bridge is defined as an arylene bridge when p=q=0, the bridge is defined as an aralkylene bridge when p+q>1.

Examples of the structural unit E-R-E' are methanolate, ethanolate, I-propanolate, benzyl alcoholate, 2-methoxyethanolate, 2-(2-piperidyl)ethanolate, 2,2,2-trifluoroethanolate, 1,1,1,3,3,3-hexafluoroisopropanolate, 2,4-(methylmercapto)ethanolate, 3-dimethylphosphanyl phenolate, 2-dimethylaminocyclohexanolate, ethyl thiolate, benzyl thiolate, 2-methoxyethane thiolate, methyl selenate, N-methyl anilide, 6-methoxy-2,3-dihydroindolate, phenolate, quinolin-7-olate, 3-methoxyphenolate, 3,5-methoxyphenolate, 3-methyl-4-dimethylamino-phenolate, 3-dimethylaminophenolate, 2-fluorophenolate, pentafluorophenolate, 3-tert-butyl-phenotate, 2,6-di-tert-butyl-4-methyl phenolate, 3-methylmercapto phenolate, 3,5-trifluoromethyl phenolate, 3,5-dimethoxyphenolate, 2-(2-pyridyl)phenolate, 6-methoxyindolate, 2'-methoxybiphenyl-2-olate, 2'-methoxy-1-1'-binaphthalenyl-2-olate or 8-methoxy-2-naphtholate.

Two ERE' units can also form one or more rings by combining with one another, such as 6,6'-di-tert-butyl-4,4'-dimethyl-2,2'-methanediyl-di-phenolate or 6,6'-di-tert-butyl-4,4'-dimethyl-2,2'-sulfanediyl-di-phenolate.

In the process according to the present invention, compounds corresponding to the formula (I) are preferably used, in which X: represents a halide or sulfonate, more preferably a sulfonate, and most preferably a perfluoroalkyl sulfonate;

M: represents boron, aluminum or gallium, and preferably aluminum;

E: represents O, S, or $NR^1$, and preferably O;

R: represents an arylene radical or an alkylene radical, and preferably phenylene;

E': represents a hydrogen (H) atom, a $R^2O$— group, a $R^2S$— group, a $R^2R^3N$— group, a $R^2R^3P$— group or a NC— group, and preferably a hydrogen (H) atom, a $R^2O$— group, a $R^2S$— group, a $R^2R^3N$— group or a $R^2R^3P$— group.

The metal compounds corresponding to the formula (I) are in some cases novel compounds and in some cases known compounds. The known compounds may be synthesized as described in the literature (see, for example, J. Indian Chem. Soc. 62 (1985) 494). The novel compounds have the formula (XI)

$$(R^FSO_3)_2M(ERE'_f) \qquad (XI)$$

as defined below, and can be obtained by reacting compounds corresponding to the formula (XII)

$$MY^1Y^2Y^3 \qquad (XII)$$

as defined below, with $H(E$—$R$—$E'_f)$ and $R^FSO_3H$; or by reacting compounds corresponding to the formula (XIII)

$$M(ERE'_f)_3 \qquad (XIII)$$

as defined below, with $R^FSO_3H$.

The polyaddition reaction catalyzed by the compounds corresponding to the formula (I) generally takes place within the temperature range 40 to 200° C., preferably within the range 40 to 160° C., more preferably 50 to 150° C., at total pressures of from 0 to 20 bar. The process may or may not be carried out in an inert organic solvent such as, for example, cyclohexane, toluene, xylene, diethylether, dimethoxyethane and/or chlorinated hydrocarbons such as methylene chloride, chloroform or 1,2-dichloropropane. The quantity of solvent is normally approximately from 10 to 30% by weight, based on the weight of polyether polyol to be prepared.

The concentration of catalyst is selected such that the polyaddition reaction is controllable effectively under the given reaction conditions. The concentration of catalyst is generally within the range 0.00005% by weight to 10% by weight, preferably within the range 0.0001% by weight to 5% by weight, based on the total weight of polyether polyol to be prepared.

The reaction times for the polyaddition reaction are within the range of a few minutes to a number of days, preferably within a few minutes to a number of hours.

The molecular weights of the polyethers prepared by the process according to the invention are within the range 100 to 20,000 g/mole, preferably within the range 200 to 15,000 g/mole. As used herein, all molecular weights referred to are number average molecular weights, based on OH numbers and determined by end-group analysis. Because of the stability of the compounds corresponding to the formula (I), in particular the triflates, used as the catalyst, vis-à-vis compounds having active hydrogen atoms (such as, for example, water, alcohols), no special materials such as, for example, enamels, need be used in the reaction apparatus which is employed.

The polyaddition process may be carried out in a continuous, a batch, or a semi-batch manner.

The process according to the invention may generally be carried out as follows:

In order to prepare polyether polyols by a polyaddition reaction between alkylene oxides and starting compounds by catalysis with Lewis acid catalysts corresponding to the formula (I), the catalyst, a starting compound (e.g. propylene glycol or trimethylolpropane) and, optionally a solvent were each introduced into a reaction vessel and were then brought to the desired reaction temperature (preferably 50 to 150° C.) at total pressures of from 0 to 20 bar. The desired quantity of alkylene oxide, preferably propylene oxide, was then dispensed continuously into the reaction vessel by means of a controlled membrane pump. After completion of the epoxide dispensing and the post-reaction time at the given reaction temperature, volatile constituents were distilled off at 90° C. for 30 minutes at reduced pressure (1 mbar) and then the reaction mixture was cooled to room temperature. The polyether polyols obtained are colorless liquids which are characterized by determining their OH values and their viscosities.

The process according to the invention is distinguished in that within the industrially attractive temperature range colorless polyether polyols are obtained. A particular advantage of the process according to the invention is that, due to the high activity of the catalysts they can be used in such low concentrations (50 ppm or less, based on the quantity of polyether polyol to be prepared—see examples 1–7) that it is not necessary to remove the catalyst from the finished polyether polyol.

Furthermore, the present invention provides novel bis (perfluoroalkyl-sulfonic acid) compounds of elements from Group 13 of the Periodic Table of the Elements.

These novel compounds correspond to the formula (XI):

$(R^F SO_3)_2 M(ERE'_I)$        (XI)

wherein:
$R^F$: represents a perfluoroalkyl or perfluoroaryl group;
M: represents a metal from Group 13 of the Periodic Table of the Elements;
E: represents oxygen, sulfur, selenium, $NR^1$ or $PR^1$, wherein:
$R^1$: represents a hydrogen atom, or a $C_1$–$C_{20}$ hydrocarbon radical, preferably a $C_1$–$C_{10}$ hydrocarbon radical, which may be alkyl or aryl, and wherein $R^1$ can form a ring with R;
R: represents a $C_1$–$C_{30}$ hydrocarbon bridge which may be an alkylene, arylene or aralkylene bridge;
E': represents a hydrogen atom, a $C_1$–$C_{20}$ hydrocarbon radical, preferably a $C_1$–$C_{10}$ hydrocarbon radical, which may be alkyl or aryl, $OR^2$, $NR^2R^3$, halogen, $SR^2$, or $PR^2R^3$,
wherein:
$R^2$ and $R^3$: may be the same or different, and each is independently selected from a hydrogen atom, or a $C_1$–$C_{20}$ hydrocarbon radical which may be alkyl, aryl or aralkyl, and wherein $R^2$ can form a ring with $R^3$ or R, and/or $R^3$ can form a ring with R or $R^2$,
and
I: represents an integer from 1 to 10.

Trifluoromethanesulfonic acid, pentafluoroethanesulfonic acid, heptafluoropropanesulfonic acid, heptadecanefluoroctanesulfonic acid, tridecafluoromethyl cyclohexylsulfonic acid, 5-trifluoromethyl dodecafluorohexanesulfonic acid or pentafluoro-phenylsulfonic acid, preferably trifluoromethanesulfonic acid, might be named as the optionally substituted $R^F SO_3$ the form of perfluoroalkylsulfonic or perfluoroarylsulfonic acids.

M, as defined above, is preferably boron, aluminum or gallium, and particularly preferably aluminum.

The unit ERE' as defined above is preferably methanolate, ethanolate, I-propanolate, tert-butanolate, cyclohexanolate, benzyl alcoholate, 2-methoxyethanolate, 2-(2-piperidyl) ethanolate, 2,2,2-trifluoroethanolate, 1,1,1,3,3,3-hexafluoroisopropanolate, 2-(methylmercapto)ethanolate, 3-dimethylphosphanyl phenolate, 2-dimethylaminocyclohexanolate, ethyl thiolate, benzyl thiolate, 2-methoxyethane thiolate, methyl selenate, N-methyl anilide, 6-methoxy-2,3-dihydroindolate, phenolate, quinolin-7-olate, 3-methoxyphenolate, 3,5'-methoxyphenolate, 3-methyl-4-dimethyl-aminophenolate, 3-dimethylaminophenolate, 2-fluorophenolate, pentafluorophenolate, 3-tert-butyl phenolate, 2,6-di-tert-butyl-4-methyl phenolate, 3-methylmercaptophenolate, 3,5-bis(trifluoromethyl)phenolate, 3,5-dimethoxy-phenolate, 2-(2-pyridyl)phenolate, 6-methoxyindolate, 2'-methoxybiphenyl-2-olate, 2'-methoxy-1,1'-binaphthalenyl-2-olate or 8-methoxy-2-naphtholate, and more preferably 1,1,1,3,3,3-hexafluoro-isopropanolate, phenolate, 3-methoxyphenolate, 3,5-methoxyphenolate, 3-methyl-4-dimethylamino-phenolate, 3-(N,N-dimethylamino)phenolate, 3-fluorophenolate, pentafluorophenolate, 3-methylmercaptophenolate, 3,5-bis(trifluoromethyl)phenolate, 3,5-dimethoxyphenolate or 6-methoxyindolate.

Individually the following compounds might be mentioned as examples: aluminum bis (trifluoromethanesulfonate) phenolate, aluminum bis (trifluoromethanesulfonate)-3-methyl-4-N,N-dimethylaminophenolate, aluminum bis (trifluoromethanesulfonate)-3-N,N-dimethylaminophenolate, aluminum bis (trifluoromethanesulfonate)-3-methoxyphenolate, aluminum bis(trifluoromethanesulfonate)-3-fluorophenolate, aluminum bis(trifluoromethanesulfonate)-3,5-difluorophenolate, aluminum bis (trifluoromethanesulfonate)-pentafluorophenolate, aluminum bis(trifluoromethanesulfonate)-6-methoxyindolate, aluminum bis(trifluoromethanesulfonate)-5-tert-butyl phenolate, aluminum bis (trifluoromethane-sulfonate)-3,5-di-tert-butyl phenolate, aluminum bis(trifluoromethane-sulfonate)-3,5-dimethoxyphenolate, aluminum bis(trifluoromethane-sulfonate)-3-mercaptophenolate, aluminum bis (trifluoromethane-sulfonate)-3-methanolate, aluminum bis (trifluoromethanesulfonate)-3-ethanolate, aluminum bis (trifluoromethanesulfonate)-isopropanolate, aluminum bis (trifluoromethanesulfonate)-3-tert-butylate, aluminum bis (trifluoromethanesulfonate)-3-benzylate, aluminum, bis (trifluoromethanesulfonate)-3-cyclohexanolate or aluminum bis(trifluoromethane-sulfonate)-3-methoxycyclohexanolate.

A process for the preparation of novel bis (perfluoroalkylsulfonic acid) compounds of the elements from Group 13 of the Periodic Table of the Elements corresponding to the formula (XI) has also been found. This process comprises (A) reacting at temperatures of from −100 to 300° C. in a first step, (1) compounds corresponding to the formula (XII):

$$MY^1Y^2Y^3 \quad (XII)$$

wherein:
  M: represents a metal from Group 13 of the Periodic Table of Elements;
  and
  $Y^1$, $Y^2$ or $Y^3$: may be the same or different, and are each independently selected from a hydrogen atom, a $C_1$–$C_{10}$ hydrocarbon which may be an alkyl or aryl group, a halide or an amide,
with (2) a compound corresponding to the formula:

$$H(ERE'_I)$$

wherein:
  E: represents oxygen, sulfur, selenium, $NR^1$ or $PR^1$,
    wherein:
      $R^1$: represents a hydrogen atom, or a $C_1$–$C_{20}$ hydrocarbon radical, preferably a $C_1$–$C_{10}$ hydrocarbon radical, which may be alkyl or aryl, and wherein $R^1$ can form a ring with R;
  R: represents a $C_1$–$C_{30}$ hydrocarbon bridge which may be an alkylene, an arylene or an aralkylene bridge;
  E': represents a hydrogen atom, a $C_1$–$C_{20}$ hydrocarbon radical, preferably a $C_1$–$C_{10}$ hydrocarbon radical, which may be alkyl or aryl, $OR^2$, $NR^2R^3$, halogen, $SR^2$, $PR^2R^3$,
    wherein:
      $R^2$ and $R^3$: may be the same of different and each is independently selected from a hydrogen atom, or a $C_1$–$C_{20}$ hydrocarbon radical which may be alkyl, aryl or aralkyl, wherein $R^2$ can form a ring with $R^3$ or R, and/or $R^3$ can form a ring with $R^2$ or R;
  and
  I: represents an integer from 1 to 10;
in the presence or absence of inert solvents, and are then (B) reacted in the second step at temperatures of from −100° C. to 300° C., with (3) a compound corresponding to the formula:

$$R^FSO_3H$$

wherein:
  $R^F$: represents a perfluoroalkyl or perfluoroaryl radical;
in the presence or absence of inert solvents. It is unimportant here whether or not the products of the first stage are isolated.

Another process for the preparation of the novel bis(perfluoroalkylsulfonic acid) compounds of the elements from Group 13 of the Periodic Table, corresponding to the formula (XI):

$$(R^FSO_3)_2M(ERE'_I) \quad (XI)$$

wherein:
  $R^F$, M, E, R, E' and I are defined as above,
and the process comprises (A) reacting, at temperatures of from −100° C. to 300° C., (1) compounds corresponding to the formula (XIII)

$$M(ERE'_I)3 \quad (XIII)$$

wherein:
  M: represents a metal from Group 13 of the Periodic Table of the Elements;
  E: represents oxygen, sulfur, selenium, $NR^1$ or $PR^1$,
    wherein:
      $R^1$: represents a hydrogen atom or a $C_1$–$C_{20}$ hydrocarbon radical, preferably a $C_1$–$C_{10}$ hydrocarbon radical, which may be alkyl or aryl, and wherein $R^1$ can form one or more rings with R;
  R: represents a $C_1$–$C_{30}$ hydrocarbon bridge which may be an alkylene, arylene or aralkylene bridge;
  E': represents a hydrogen atom, a $C_1$–$C_{20}$ hydrocarbon radical, preferably a $C_1$–$C_{10}$ hydrocarbon radical, which may be alkyl or aryl, $OR^2$, $NR^2R^3$, halogen, $SR^2$, or $PR^2R^3$, wherein:
      $R^2$ and $R^3$: may be the same or different, and each is independently selected from a hydrogen atom, a $C_1$–$C_{20}$ hydrocarbon radical which may be alkyl, aryl, or aralkyl, and wherein $R^2$ can form a ring with $R^3$ or R, and/or $R^3$ can form a ring with $R^2$ or R;
  and
  I: represents an integer from 1 to 10;
with (2) a compound corresponding to the formula:

$$R^FSO_3H$$

wherein:
  $R^F$: represents a perfluoroalkyl or a perfluoroaryl group;
in the presence or absence of one or more inert solvents.

Aluminum trichloride, aluminum tribromide, trimethyl aluminum, triethyl aluminum, triisobutyl aluminum, diethyl aluminum chloride or ethyl aluminum sesquichloride, for example, are preferably used as the compound corresponding to the formula (XII) in the process according to the invention.

Aluminum triisopropoxide, aluminum tri-tert-butoxide or aluminum triphenolate, for example, are preferably used as the compounds corresponding to the formula (XIII) in the process according to the invention.

A preferred temperature range of −100° C. to 200° C., and more preferably from −80 to 150° C., are suggested for the above processes. The total reaction time varies depending on the raw materials, anywhere from between a few minutes and 48 hours. It is also optionally possible to work at elevated or reduced pressure.

The process according to the invention is preferably carried out in the presence of one or more solvents, preferably such as, for example, hexane, heptane, octane, other aliphatic hydrocarbons, cyclohexane, methylcyclohexane, benzene, toluene, xylene, methylene chloride, dichloroethane, trichloroethane, chlorobenzene, dichlorobenzene, trichlorobenzene or mixtures thereof in any ratio.

The quantity of solvent or solvent mixture may vary at will. It is expediently selected such that the concentration of the reactants is between 5 and 80% by weight, based on the total reaction mixture.

The following are possible variations of the preferred embodiment of the process according to the invention, and specifically, of the reaction of the compound corresponding to the formula (XII) with $H(ERE'_I)$ and $R^FSO_3H$. First, the compound corresponding to the formula (XII) is dissolved or suspended in the solvent or solvent mixture, and is brought to the required reaction temperature. $H(ERE'_I)$ is dispensed into the suspension, either in solution or as a pure substance, within suitable periods of time, such that the temperature and the gas evolved remain within the suitable range. The reaction mixture is then allowed to continue to react at a suitable reaction temperature until no further gas evolves. The reaction mixture is then brought to the required temperature, and the perfluoroalkylsulfonic or perfluoroarylsulfonic acid is dispensed-in, either in solution or as a pure substance, within suitable periods of time, such that the temperature and gas evolved remain within the suitable range. Then, the reaction mixture is allowed to continue to react at a suitable reaction temperature until no further gas evolves.

The solvent may be removed from the reaction mixture by distillation, or in some cases the product corresponding to the formula (XI) may be advantageously filtered off or centrifuged off.

The compounds used according to the invention as raw materials represent known products some of which are obtainable commercially.

Owing to the manner of their preparation the compounds according to the invention may contain varying amounts of solvent.

The compounds according to the invention are suitable as catalysts for the synthesis of polyethers by ring-opening polymerization of cyclic ethers. Here, cyclic ethers are understood to be compounds such as, for example, oxiranes, oxetanes, tetrahydrofurans, oxepanes, 1,3-dioxolanes or 1,3,5-trioxanes.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

Synthesis of the Aluminum Compounds

A) Synthesis of Aluminum bis(Trifluoromethanesulfonate) Phenolate:

At −78° C., a solution of 1.30 g (10.0 mmol) phenol in methylene chloride was added dropwise to 5.00 ml of a 2.00 molar solution of trimethyl aluminum (10.0 mmol) in toluene. The reaction mixture was heated to 0° C. and stirred for approx. 30 minutes until no further gas was observed to evolve. The reaction mixture was then cooled again to −78° C., and 1.77 ml (=3.00 g; 20.0 mmol) trifluoromethanesulfonic acid was added dropwise. The reaction mixture was then heated slowly to room temperature and stirred for 16 hours. The solvent was removed under vacuum, and the product was dried under a high vacuum. Yield: 4.18 g B) Synthesis of Aluminum bis(Trifluoromethanesulfonate)-3.5-di-tert-butyl Phenolate:

At −78° C. a solution of 2.06 g (10.0 mmol) 3,5-di-tert.-butyl phenol in methylene chloride was added dropwise to 5.00 ml of a 2.00 molar solution of trimethyl aluminum (10.0 mmol) in toluene. The reaction mixture was heated to 0° C. and stirred for approx. 30 minutes until no further gas was observed to evolve. The reaction mixture was then cooled again to −78° C., and 1.77 ml (=3.00 g; 20.0 mmol) trifluoromethanesulfonic acid was added dropwise. The reaction mixture was then heated slowly to room temperature and stirred for 16 hours. The product was filtered off, washed with methylene chloride and dried under a high vacuum. Yield: 3.34 g.

C) Synthesis of Aluminum bis(Trifluoromethanesulfonate)-3-dimethylaminophenolate:

At −78° C. a solution of 1.37 g (10.0 mmol) 3-dimethylaminophenol in methylene chloride was added dropwise to 5.00 ml of a 2.00 molar solution of trimethyl aluminum (10.0 mmol) in toluene. The reaction mixture was heated to 0° C. and stirred for approx. 30 minutes until no further gas was observed to evolve. The mixture was then cooled again to −78° C., and 1.77 ml (=3.00 g; 20.0 mmol) trifluoromethanesulfonic acid was added dropwise. The reaction mixture was then heated slowly to room temperature and stirred for 16 hours. The solvent was removed under vacuum, and the product was dried under a high vacuum. Yield: 4.25 g.

D) Synthesis of Aluminum bis(Trifluoromethanesulfonate)-3-methoxyphenolate:

At −78° C. a solution of 1.24 g (10.0 mmol) 3-methoxyphenol in methylene chloride was added dropwise to 137 ml (1.14 g: 10 mmol) triethyl aluminum in methylene chloride. The reaction mixture was heated to 0° C. and stirred for approx. 30 minutes until no further gas was observed to evolve. The reaction mixture was then cooled again to −78° C. and 1.77 ml (=3.00 g; 20.0 mmol) trifluoromethanesulfonic acid was added dropwise. The reaction mixture was then heated slowly to room temperature and stirred for 16 hours. The product was filtered off, washed with methylene chloride and dried under a high vacuum. Yield: 3.89 g.

E) Synthesis of aluminum bis(trifluoromethanesulfonate)-3.5-dimethoxyphenolate:

A suspension of 1.33 g (10.0 mmol) aluminum trichloride and 1.54 g (10.0 mmol) 3,5-dimethoxyphenol in toluene was heated for 2 hours under reflux until no further gas was observed to evolve. The reaction mixture was cooled to 0° C., 1.77 ml (=3.00 g; 20.0 mmol) trifluoromethanesulfonic acid was added dropwise, and the mixture was stirred for 16 hours. The solvent was removed under vacuum and the residue was taken up in methylene chloride, after which the product was precipitated by the addition of hexane, filtered off, washed with hexane and dried under a high vacuum. Yield: 4.68 g.

F) Synthesis of Aluminum bis(Trifluoromethanesulfonate) pentafluorophenolate:

At −78° C. a solution of 3.68 g (20.0 mmol) pentafluorophenol in methylene chloride was added dropwise to 10.0 ml of a 2.00 molar solution of trimethyl aluminum (20.0 mmol) in toluene. The reaction mixture was heated to 0° C. and stirred for approx. 30 minutes until no further gas was observed to evolve. The reaction mixture was then cooled again to −78° C. and 3.54 ml (=6.00 g; 40.0 mmol) trifluoromethanesulfonic acid are added dropwise. The reaction mixture was then heated slowly to room temperature and stirred for 16 hours. The product was filtered off, washed with methylene chloride and dried under a high vacuum. Yield: 8.71 g.

G) Synthesis of Aluminum bis(Trifluoromethanesulfonate)-4-dimethyl Amino-3-methylphenolate):

At −78° C. a solution of 5.00 ml of a 2.00 molar solution of trimethyl aluminum (10.0 mmol) in toluene was added dropwise to 1.50 (10.0 mmol) 6-dimethylamino-3-hydroxytoluene in methylene chloride. The reaction mixture was heated to 0° C. and stirred for approx. 30 minutes until no further gas was observed to evolve. The reaction mixture was then cooled again to −78° C., and 1.77 ml (=3.00 g; 20.0 mmol) trifluoromethane-sulfonic acid was added dropwise. The reaction mixture was then heated slowly to room temperature and stirred for 16 hours. The solvent was removed under vacuum, and the product was dried under a high vacuum. Yield: 4.75 g.

H) Synthesis of Aluminum bis(Trifluoromethanesulfonate) hexafluoroisopropanolate:

At −78° C. a solution of 1.05 ml (=1.68 g; 10.0 mmol) hexafluoroisopropanol in methylene chloride was added dropwise to 5.00 ml of a 2.00 molar solution of trimethyl aluminum (10.0 mmol) in toluene. The reaction mixture was heated to 0° C. and stirred for approx. 30 minutes until no further gas evolution was discernible. The reaction mixture was then cooled again to −78° C., and 1.77 ml (=3.00 g; 20.0 mmol) trifluoromethanesulfonic acid was added dropwise. The reaction mixture was then heated slowly to room temperature and stirred for 16 hours. The product was filtered off, washed with methylene chloride and dried under a high vacuum. Yield: 4.27 g.

I) Synthesis of Aluminum bis(Trifluoromethanesulfonate)-3,3-dioxobenz-1,3-oxathiol-5-olate):

At −78° C. a solution of 1.86 g (10.0 mmol) 3,3-dioxobenz-1,3-oxathiol-5-ol in methylene chloride was added dropwise to 5.00 ml of a 2.00 molar solution of trimethyl aluminum (10.0 mmol) in toluene. The reaction mixture was heated to 0° C. and stirred for approx. 30 minutes until no further gas was observed to evolve. The reaction mixture was then cooled again to −78° C., and 1.77 ml (=3.0 g; 20.0 mmol) trifluoromethanesulfonic acid are added dropwise. The reaction mixture was then heated slowly to room temperature and stirred for 16 hours. The product was filtered off, washed with methylene chloride and dried under a high vacuum. Yield: 5.33 g.

J) Synthesis of Aluminum bis(Trifluoromethanesulfonate)-3-methylmer-captophenolate:

At −78° C. a solution of 2.00 g (7.1 mmol) 3-methylmercaptophenol in methylene chloride was added dropwise to 0.97 ml (0.81 g; 7.1 mmol) triethyl aluminum in methylene chloride. The reaction mixture was heated to 0° C. and stirred for approx. 30 minutes until no further gas was observed to evolve. The reaction mixture was then cooled again to −78° C., and 1.26 ml (=2.13 g; 14.2 mmol) trifluoromethanesulfonic acid was added dropwise. The reaction mixture was then heated slowly to room temperature and stirred for 16 hours. The product was filtered off, washed with methylene chloride and dried under a high vacuum. Yield: 3.07 g.

K) Synthesis of Aluminum bis(Trifluoromethanesulfonate)-tert.-butanolate:

At −78° C. a solution of 0.96 ml (=0.74 g; 10.0 mmol) tert-butanol in toluene was added dropwise to 5.00 ml of a 2.00 molar solution of trimethyl aluminum (10.0 mmol) in toluene. The reaction mixture was heated to 0° C. and stirred for approx. 30 minutes until no further gas was observed to evolve. The reaction mixture was then cooled again to −78° C., and 1.77 ml (=3.00 g; 20.0 mmol) trifluoromethanesulfonic acid was added dropwise. The reaction mixture was then heated slowly to room temperature and stirred for 16 hours. The solvent was removed under vacuum, and the product was dried under a high vacuum. Yield: 3.97 g.

Example 1

87.7 g. trimethylolpropane and 8 mg aluminum bis(trifluoromethanesulfonate) phenolate were placed under protective gas (argon, slight overpressure (0.2 bar)) in a 500 ml compression glass autoclave and heated to 130° C., with stirring. 112.3 g propylene oxide were then dispensed-in continuously by means of a temperature- and pressure-controlled membrane pump at a temperature of 130° C. and at a constant pressure of 2.5 bar (absolute). The reaction time was 29 minutes. After complete dispensing of the propylene oxide and 2 hours' post-reaction time at 130° C., volatile constituents were distilled off at 90° C. (1 mbar) and then cooled to room temperature.

| Polyether polyol: | Color: | colorless, clear |
| --- | --- | --- |
| | OH value (mg KOH/g): | 531 |
| | Viscosity (mPa · s at 25° C.): | 1351 |

Example 2

Example 1 was repeated, but using 8 mg aluminum bis(trifluoro-methanesulfonate)-3,5-di-tert-butylphenolate.

| Reaction time: | 27 minutes | |
| --- | --- | --- |
| Polyether polyol: | Color: | colorless, clear |
| | OH value (mg KOH/g): | 526 |
| | Viscosity (mPa · s at 25° C.): | 1308 |

Example 3

Example 1 was repeated, but using 8 mg aluminum bis(trifluoro-methanesulfonate)-3-methoxyphenolate.

| Reaction Time: | 32 minutes | |
| --- | --- | --- |
| Polyether polyol: | Color: | colorless, clear |
| | OH value (mg KOH/g): | 535 |
| | Viscosity (mPa · s at 25° C.): | 1314 |

Example 4

Example 1 was repeated, but using 8 mg aluminum bis(trifluoro-methanesulfonate)-3,5-dimethoxyphenolate.

| Reaction time: | 26 minutes | |
| --- | --- | --- |
| Polyether polyol: | Color: | colorless, clear |
| | OH value (mg KOH/g): | 525 |
| | Viscosity (mPa · s at 25° C.): | 1311 |

Example 5

Example 1 was repeated, but using 8 mg aluminum bis(trifluoro-methanesulfonate)-3-methylmercaptophenolate.

| Reaction time: | 44 minutes | |
| --- | --- | --- |
| Polyether polyol: | Color: | colorless, clear |
| | OH value (mg KOH/g): | 535 |
| | Viscosity (mPa · s at 25° C.): | 1353 |

Example 6

Example 1 was repeated, but using 8 mg aluminum bis(trifluoro-methanesulfonate) pentafluorophenolate.

| Reaction time: | 24 minutes | |
| --- | --- | --- |
| Polyether polyol | Color: | Colorless, clear |
| | OH value (mg KOH/g): | 531 |
| | Viscosity (mPa · s at 25° C.): | 1330 |

Example 7

Example 1 was repeated, but using 8 mg aluminum bis(trifluoro-methanesulfonate)-3,3-dioxobenz-1,3-oxathiol-5-olate.

| Reaction time: | 24 minutes | |
| --- | --- | --- |
| Polyether polyol: | Color: | colorless, clear |

| | |
|---|---|
| OH value (mg KOH/g): | 533 |
| Viscosity (mPa · s at 25° C.): | 1343 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A compound corresponding to the formula (XI)

$$(R^F SO_3)_2 M(ERE'_I) \quad (XI)$$

wherein:
$R^F$: represents a perfluoroalkyl or perfluoroaryl group;
M: represents a metal from Group 13 of the Periodic Table of the Elements;
E: represents oxygen, sulfur, selenium, $NR^1$ or $PR^1$,
  wherein:
    $R^1$: represents a hydrogen atom or a $C_1-C_{20}$ hydrocarbon radical which may be alkyl or aryl, wherein $R^1$ can form a ring with R;
R: represents a $C_1-C_{30}$ hydrocarbon bridge which may be an alkylene, arylene or aralkylene bridge;
E': represents a hydrogen atom, a $C_1-C_{20}$ hydrocarbon radical which may be alkyl or aryl, $OR^2$, $NR^2R^3$, halogen, $SR^2$ or $PR^2R^3$,
  wherein:
    $R^2$ and $R^3$: may be the same or different and each represents a hydrogen atom, or a $C_1-C_{20}$ hydrocarbon radical which may be alkyl, aryl or aralkyl, wherein $R^2$ can form a ring with $R^3$ or R and/or $R^3$ can form a ring with R or $R^2$, and
I: represents an integer from 1 to 10.

2. A process for the preparation of a compound corresponding to formula (XI) of claim 1, comprising (A) first reacting (1) a compound corresponding to the formula (XII)

$$MY^1Y^2Y^3 \quad (XII)$$

wherein:
M: represents a metal from Group 13 of the Periodic Table of the Elements;
$Y^1$, $Y^2$ or $Y^3$: are the same or different and each is independently selected from the group consisting of a hydrogen atom, a $C_1-C_{10}$ hydrocarbon radical which may be alkyl or aryl, a halide or an amide,
with (2) a compound corresponding to the formula $$H(ERE'_I)$$

wherein:
E: represents oxygen, sulfur, selenium, $NR^1$ or $PR^1$,
wherein:
$R^1$: represents a hydrogen atom or a $C_1-C_{20}$ hydrocarbon radical which may be alkyl, aryl, wherein $R^1$ can form a ring with R,
R: represents a $C_1-C_{30}$ hydrocarbon bridge which may be an alkylene, arylene or aralkylene bridge,
E': represents a hydrogen atom, a $C_1-C_{20}$ hydrocarbon radical which may be alkyl or aryl, $OR^2$, $NR^2R^3$, halogen, $SR^2$, $PR^2R^3$, wherein:
$R^2$ and $R^3$: may be the same or different and each is independently selected from a hydrogen atom or a $C_1-C_{20}$ hydrocarbon radical which may be alkyl, aryl or aralkyl, wherein $R^2$ can form a ring with $R^3$ or R and/or $R^3$ can form a ring with R or $R^2$; and
I: represents an integer from 1 to 10;
at temperatures of from −100° C. to 300° C., in the presence or absence of inert solvents, and (B) then reacting with $R^F SO_3 H$
wherein:
$R^F$: is perfluoroalkyl or perfluoroaryl
at temperatures of from −100° C. to 300° C. in the presence of or absence of inert solvents.

3. A process for the preparation of a compound corresponding to the formula (XI) of claim 1, wherein a compound corresponding to the formula (XIII)

$$M(ERE'_I)_3 \quad (XIII)$$

wherein:
M: represents a metal from Group 13 of the Periodic Table of the Elements;
E: represents oxygen, sulfur, selenium, $NR^1$ or $PR^1$,
  wherein:
    $R^1$: represents a hydrogen atom or a $C_1-C_{20}$ hydrocarbon radical which may be alkyl or aryl, and wherein $R^1$ can form a ring with R;
R: represents a $C_1-C_{30}$ hydrocarbon bridge which may be an alkylene, arylene or aralkylene bridge;
E': represents a hydrogen atom or a $C_1-C_{20}$ hydrocarbon radical which may be alkyl or aryl, $OR^2$, $NR^2R^3$, halogen, $SR^2$, or $PR^2R^3$, wherein:
  $R^2$ and $R^3$: are the same or different and are independently selected from a hydrogen atom or a $C_1-C_{20}$ hydrocarbon radical which may be alkyl, aryl or aralkyl, and wherein $R^2$ can form a ring with $R^3$ or R and/or $R^3$ can form a ring with R or $R^2$, and
I: denotes an integer from 1 to 10;
is reacted with $R^F SO_3 H$ at temperatures of from −100° C. to 300° C., in the presence or absence of inert solvents.

4. A process for ring-opening polymerization of cyclic esters in the presence of compounds corresponding to the formula (XI) of claim 1.

5. The process of claim 1, wherein:
$R^1$ represents a $C_1-C_{10}$ hydrocarbon radical which may be alkyl or aryl.

6. The process of claim 1, wherein:
E' represents a $C_1-C_{10}$ hydrocarbon radical which may be alkyl or aryl.

7. The process of claim 2, wherein:
$R^1$ represents a $C_1-C_{10}$ hydrocarbon radical which may be alkyl or aryl.

8. The process of claim 2, wherein:
E' represents a $C_1-C_{10}$ hydrocarbon radical which may be alkyl or aryl.

9. The process of claim 3, wherein:
$R^1$ represents a $C_1-C_{10}$ hydrocarbon radical which may be alkyl or aryl.

10. The process of claim 3, wherein:
E' represents a $C_1-C_{10}$ hydrocarbon radical which may be alkyl or aryl.

* * * * *